United States Patent
Berger et al.

(10) Patent No.: US 8,541,345 B2
(45) Date of Patent: Sep. 24, 2013

(54) COMPOSITIONS AND METHODS FOR THE IDENTIFICATION AND USE OF EPIGENETIC MARKERS USEFUL IN THE STUDY OF NORMAL AND ABNORMAL MAMMALIAN GAMETOGENESIS

(75) Inventors: Shelley L. Berger, Wayne, PA (US); Jerome Govin, Pontarlier (FR)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 185 days.

(21) Appl. No.: 12/948,552

(22) Filed: Nov. 17, 2010

(65) Prior Publication Data
US 2011/0152122 A1 Jun. 23, 2011

Related U.S. Application Data

(60) Provisional application No. 61/261,923, filed on Nov. 17, 2009.

(51) Int. Cl.
*C40B 40/06* (2006.01)
*C40B 30/06* (2006.01)
*A61K 49/00* (2006.01)

(52) U.S. Cl.
USPC .................. 506/16; 506/10; 424/9.1; 424/9.2

(58) Field of Classification Search
USPC .......................................................... 506/16
See application file for complete search history.

(56) References Cited

PUBLICATIONS

Dai et al., "Probing Nucleosome Function: A Highly Versatile Library of Synthetic Histone H3 and H4 Mutants," *Cell*, Sep. 2008, 134:1066-1078.
Govin et al., "Genome reprogramming during sporulation," *International Journal of Developmental Biology*, 2009, 53:425-432.
Hammond et al., "Distinctive chromatin in human sperm packages genes for embryo development," *Nature*, Jul. 2009, 460(23):473-479.
Metzger et al., "Phosphorylation of histone H3 at threonine 11 establishes a novel chromatin mark for transcriptional regulation," *Nature Cell Biology*, Jan. 2008, 10(1):53-60 and supplementary information pp. 1-6.
Nakanishi, et al., "A comprehensive library of histone mutants identifies nucleosomal residues required for H3K4 methylation," *Nature Structural & Molecular Biology*, Aug. 2008, 15(8):881-888.
Shimada et al., "Chk1 Is a Histone H3 Threonine 11 Kinase that Regulates DNA Damage-Induced Transcriptional Repression," *Cell*, Jan. 2008, 132:221-232.

*Primary Examiner* — Ardin Marschel
*Assistant Examiner* — Richard L Manteuffel
(74) *Attorney, Agent, or Firm* — Riverside Law LLP

(57) ABSTRACT

The invention includes compositions comprising a *S. cerevisiae* yeast library, and methods of identifying an epigenetic marker for the diagnosis of infertility or a disorder associated with gametogenesis in an individual.

11 Claims, 15 Drawing Sheets

Fig. 1D

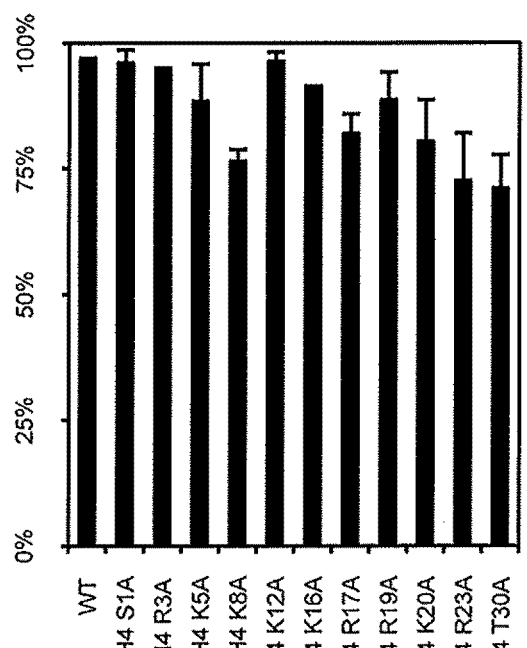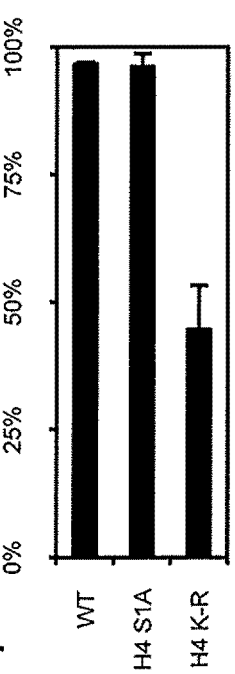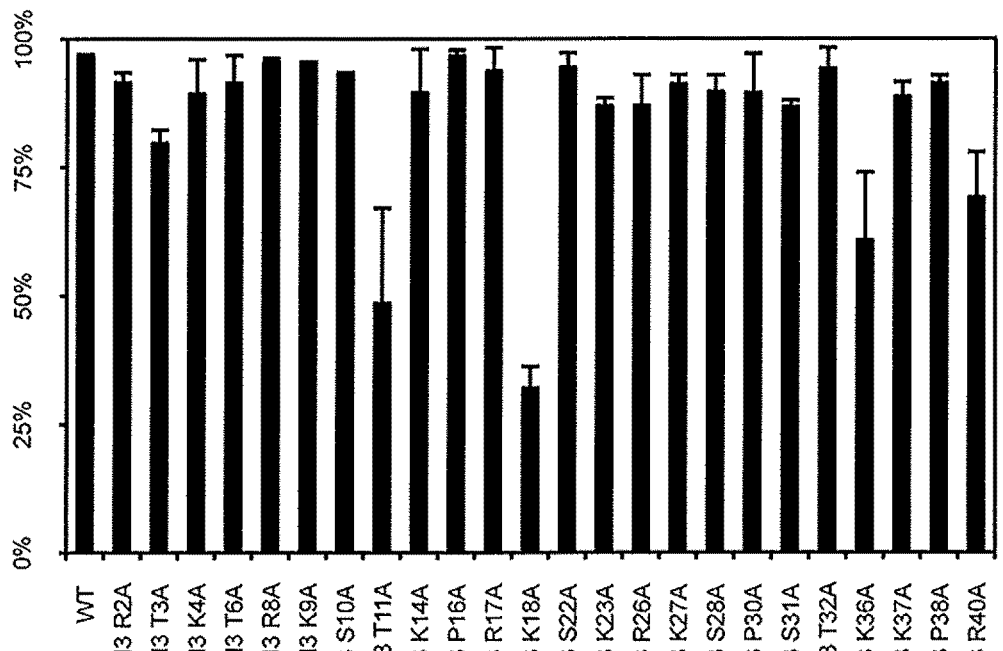
Fig. 4B
Fig. 4C
Fig. 4A

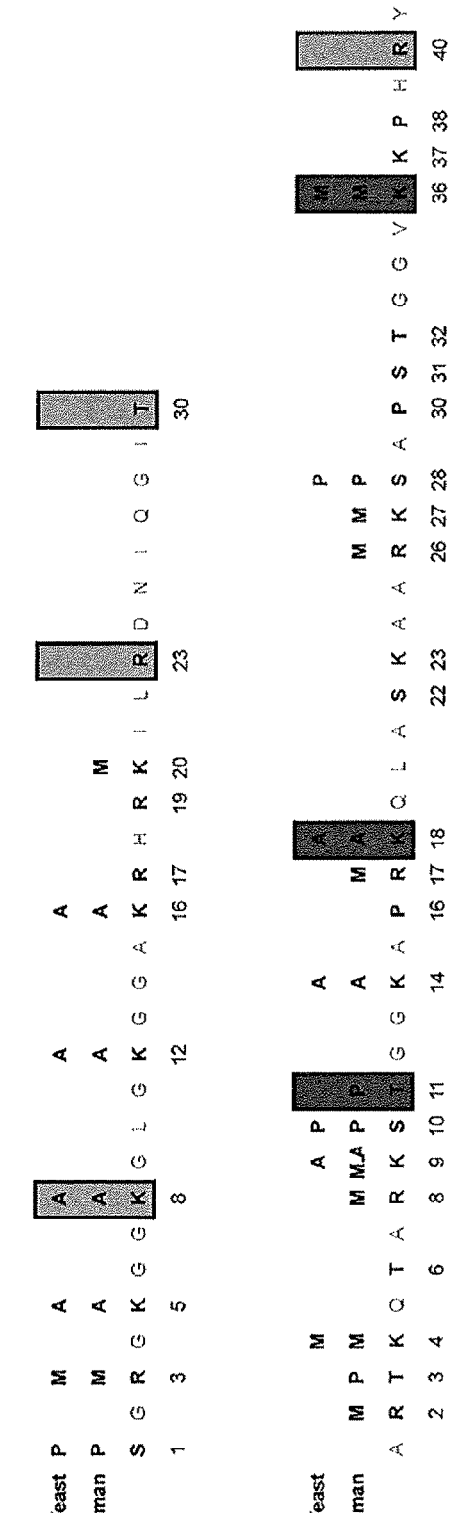

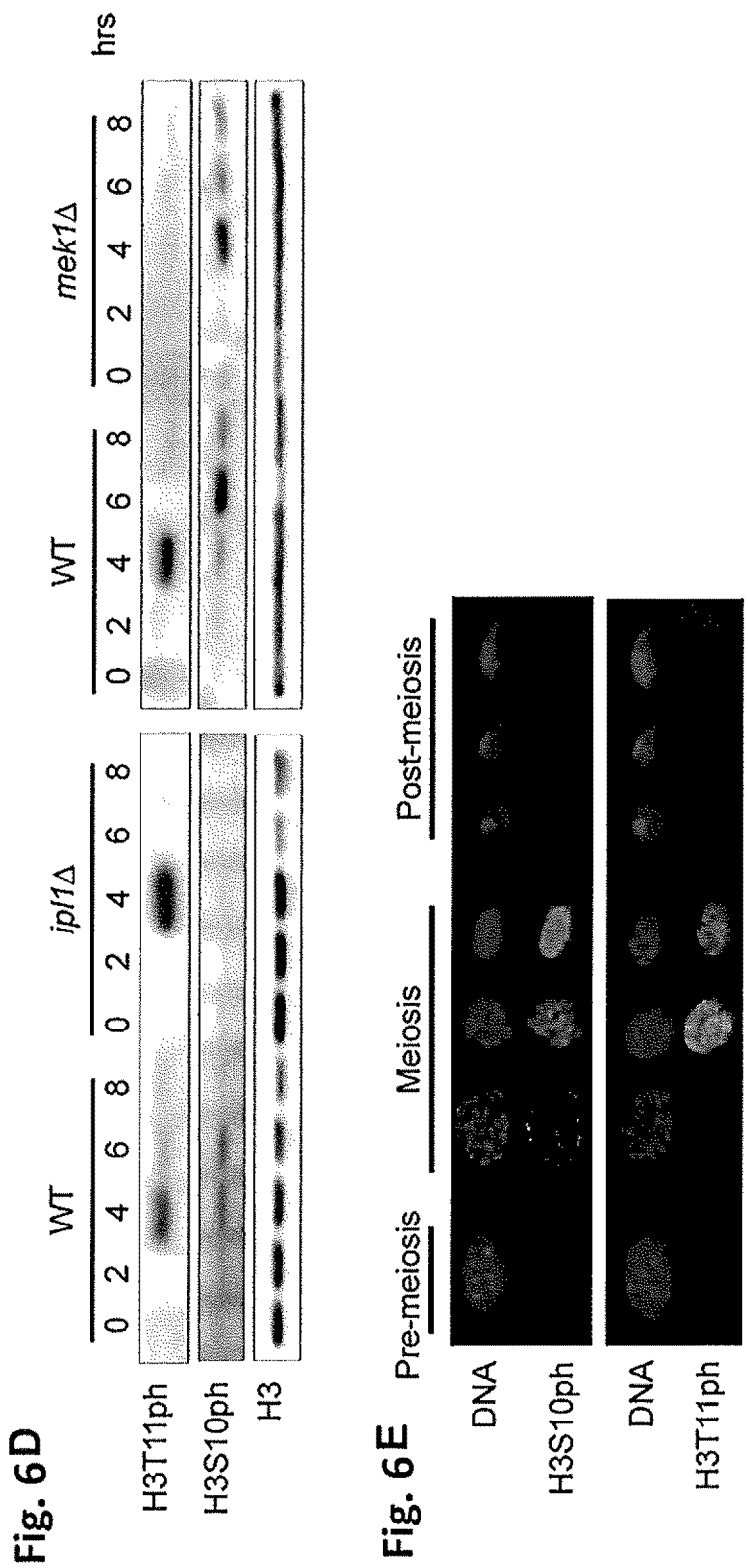

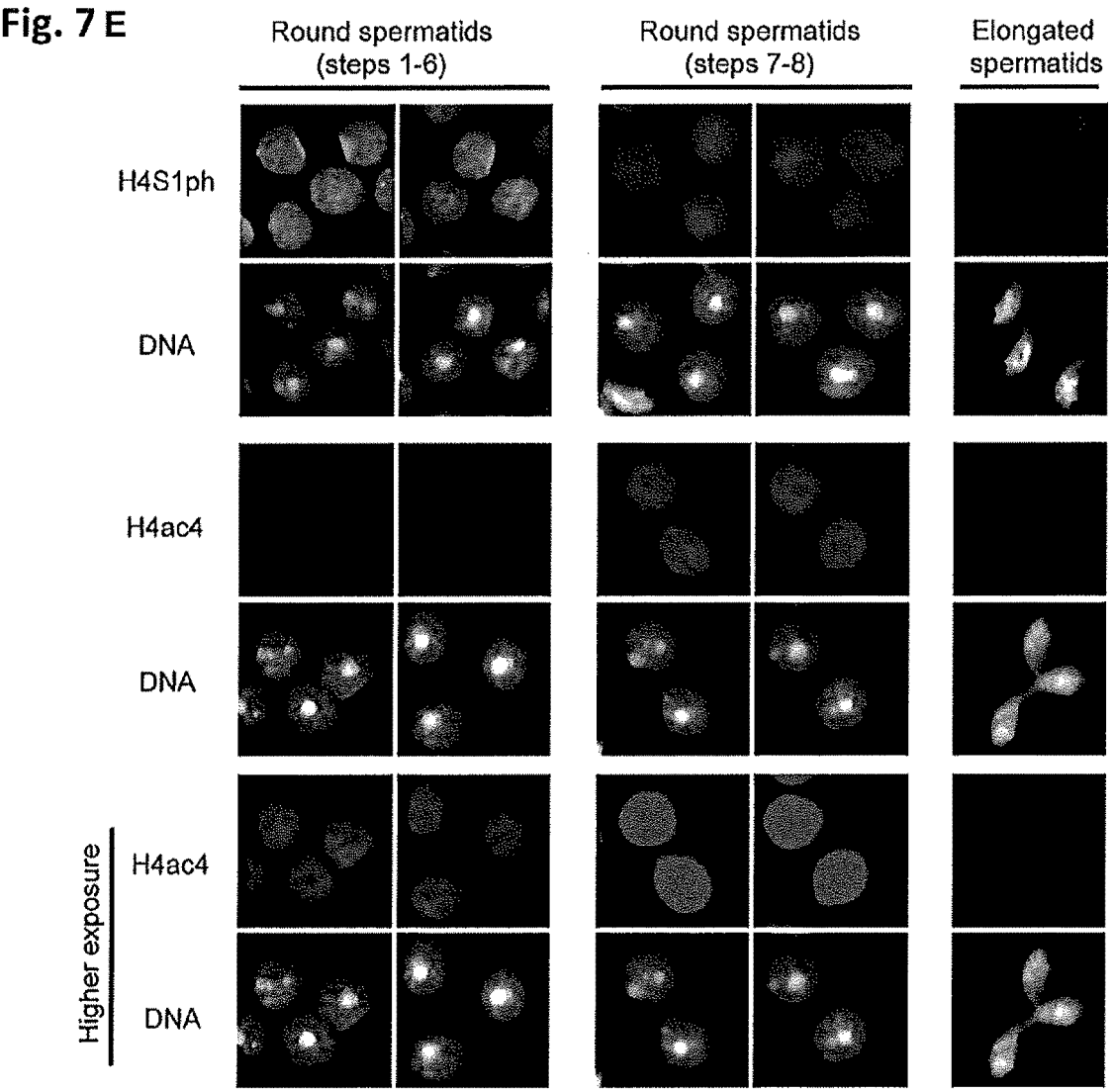

COMPOSITIONS AND METHODS FOR THE IDENTIFICATION AND USE OF EPIGENETIC MARKERS USEFUL IN THE STUDY OF NORMAL AND ABNORMAL MAMMALIAN GAMETOGENESIS

CROSS REFERENCE TO RELATED APPLICATIONS

The present claims priority to U.S. Provisional Patent Application No. 61/261,923, filed Nov. 17, 2009, which application is incorporated herein in its entirety by reference.

STATEMENT REGARDING FEDERALLY SUPPORTED RESEARCH OR DEVELOPMENT

This invention was made with government support under grant number GM55360 awarded by the National Institutes of Health. The government has certain rights in the invention.

BACKGROUND OF THE INVENTION

Epigenetic controls play a role in a variety of biological phenomena including cell differentiation, gene inactivation and silencing of foreign DNA. Rather than serving simply an organizational role for DNA packing, chromatin structure plays important roles in the epigenetic control of gene expression. Chromatin structure influences nearly all DNA-related processes, including replication, repair, recombination and transcription (Kornberg et al., 1999, Cell 98:285-94; Shilatifard, 2006, Ann. Rev. Biochem. 75:243-69; Jenuwein and Allis, 2001, Science 293:1074-80). The basic unit of chromatin is the nucleosome. A nucleosome consists of 147 base pairs of DNA wrapped around an octamer of histones that is made up of two H2A-H2B dimers and a single H3-H4 tetramer (Luger et al., 1997, Nature 389:251-60). Histones are highly conserved proteins from yeast to humans. The structure of chromatin is altered by the post-translational modification of histones (Kornberg et al., 1999, Cell 98:285-94; Shilatifard, 2006, Annu. Rev. Biochem. 75:243-69; Jenuwein & Allis, 2001, Science 293:1074-80), by interactions with other proteins such as ATP-dependent chromatin-remodeling complexes, or by replacement of core histones with histone variants (Mito et al., 2007, Science 315:1408-11; Polo, 2006, Cell 127:481-93; Lacoste & Almouzni, 2008, Nat. Cell Biol. 10:7-9). Post-translational covalent modifications of histones are known to include serine and threonine phosphorylation, lysine acetylation, lysine and arginine methylation and ubiquitination (Bhaumik et al., 2007, Nat. Struct. Mol. Biol. 14:1008-16; Berger, 2002, Curr. Opin. Genet. Dev. 12:142-48).

When environmental conditions such as nutrient depletion compromise survival, the budding yeast Saccharomyces cerevisiae induces and completes a differentiation program called sporulation. The first step consists of meiosis, which generates genetic diversity within the eventual haploid cells. The post-meiotic maturation stage reinforces protective barriers, such as the spore wall, against deleterious external conditions. The sporulation differentiation program involves many chromatin-related events, including execution of a precise transcription program involving more than one thousand genes. In later stages of yeast sporulation, the spore nucleus becomes highly compacted, sharing certain characteristics with the metazoan male gamete, the spermatozoon. In addition, yeast sporulation follows a sequence of events similar to that of higher eukaryotic spermatogenesis. In both cases, genetic information is recombined during meiosis, and then compacted and stored in a unique chromatin structure (that is, compared to vegetative or somatic cells) in haploid, highly differentiated cells. Remarkably, spores germinate to restore a fully functional vegetative cell, just as gametes generate an entire new somatic organism.

There is a need in the art to elucidate the epigenetic commonalities between yeast sporulation and higher eukaryotic gametogenesis as a means of studying mammalian gametogenesis. Moreover, there exists a need in the art to identify epigenetic markers associated with mammalian infertility. The present invention satisfies these needs.

BRIEF SUMMARY OF THE INVENTION

The invention includes a composition comprising an *S. cerevisiae* strain SK1 yeast library, wherein each member of the yeast library has histone H3 and histone H4 deleted from its genome; and wherein the wild-type historic sequence of one of the two histones H3 and H4 is expressed from a plasmid; and wherein the remaining one of the two wild-type histone sequences that is not expressed from a plasmid is substituted with a mutant histone sequence expressed from a plasmid; and wherein the mutant histone sequence has one of its wild-type amino acid residues substituted with alanine; and wherein each member of the yeast library has only a single mutation; and wherein each amino acid position mutation in H3 and H4 is present at least one time in the library. In one embodiment, the *S. cerevisiae* strain SK1 yeast library is the yeast library, The invention also includes a composition comprising an *S. cerevisiae* strain SK1 yeast library, wherein each member of the yeast library has histone H2A and histone H2B deleted from its genome; and wherein the wild-type histone sequence of one of the two histones H2A and H2B is expressed from a plasmid; and wherein the remaining one of the two wild-type histone sequences that is not expressed from a plasmid is substituted with a mutant histone sequence expressed from a plasmid; and wherein the mutant histone sequence has one of its wild-type amino acid residues substituted with alanine; and wherein each member of the yeast library has only a single mutation; and wherein each amino acid position mutation in H2A and H2B is present at least one time in the library. In one embodiment, the *S. cerevisiae* strain SK1 yeast library is the yeast library.

The invention further includes a composition comprising an *S. cerevisiae* strain SK1 yeast library, wherein each member of the yeast library has histone H2A, histone H2B, histone H3 and histone H4 deleted from its genome; and wherein the wild-type histone sequence of three of the four histones H2A, H2B, H3, and H4 is expressed from a plasmid; and wherein the remaining one of the four wild-type historic sequences that is not expressed from a plasmid is substituted with a mutant histone sequence expressed from a plasmid; and wherein the mutant histone sequence has one of its amino acid residues substituted with alanine; and wherein each member of the yeast library has only a single mutation; and wherein each amino acid position mutation in H2A, H2B, H3 and H4 is present at least one time in the library. In one embodiment, the *S. cerevisiae* strain SK1 yeast library is the yeast library.

The invention also includes a method of identifying an epigenetic marker for diagnosis of infertility or a disorder associated with gametogenesis. The method comprises the step of creating an *S. cerevisiae* strain SK1 yeast library of mutant histones. The method also comprises the step of inducing sporulation. The method also comprises the step of assessing efficiency of the sporulation in individual mutants. The method also comprises the step of identifying particular amino acid positions of the mutants with diminished efficiency of the sporulation. The method also comprises the step of evaluating epigenetic modifications at the amino acid positions. The method also comprises the step of evaluating epigenetic modifications at the same amino acid position of a mammalian histone. When the epigenetic modification state of the yeast histone is the same as the mammalian histone, the epigenetic marker for the diagnosis of the infertility or the disorder associated with gametogenesis is identified.

In one embodiment, the marker is restricted to meiosis. In another embodiment, the presence of the marker during the yeast sporulation correlates with the presence of the marker during the gametogenesis. In yet another embodiment, the marker is at least one selected from the group consisting of a methylation marker, an acetylation marker, and a phosphorylation marker. In yet another embodiment, the marker is phosphorylated H3T11.

The invention further includes a composition comprising an epigenetic marker identified by the screening method described above. In one embodiment, the epigenetic marker is restricted to meiosis. In another embodiment, the presence of the epigenetic marker during yeast sporulation correlates with the presence of the epigenetic marker during mammalian gametogenesis. In yet another embodiment, the epigenetic marker is at least one selected from the group consisting of a methylation marker, an acetylation marker, and a phosphorylation marker. In yet another embodiment, the epigenetic marker is phosphorylated H3T 11. In yet another embodiment, the epigenetic marker is phosphorylated by Mek1 or a homologue thereof.

The invention also includes a method of using the epigenetic marker described above as a diagnostic marker of infertility or a disorder associated with gametogenesis in an individual. The method comprises the step of obtaining a biological sample from the individual. The method further comprises the step of assessing the biological sample for the presence of the epigenetic marker. When the epigenetic marker is present in the biological sample, the individual is diagnosed with the infertility or the disorder associated with gametogenesis.

The invention further includes a method of using the epigenetic marker described above to evaluate the progress of a therapeutic treatment modulating fertility or a disorder associated with gametogenesis in an individual. The method comprises the step of obtaining a biological sample from the individual. The method further comprises the step of assessing the biological sample for the presence of the epigenetic marker. The level of the epigenetic marker present in the biological sample is indicative of the progress of the therapeutic treatment modulating the fertility or the disorder associated with gametogenesis.

In one embodiment, the individual is mammal. In another embodiment, the mammal is a human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1D illustrates the sporulation efficiency phenotype of specific mutations (histone H4-SEQ ID NO:1; histone H3-SEQ ID NO:2).

FIG. 4A illustrates the results of an example experiment assessing sporulation efficiency of mutations in the histone H3 tail.

FIG. 4B illustrates the results of an example experiment assessing sporulation efficiency of mutations in the histone H4 tail.

FIG. 4C illustrates the results of an example experiment assessing sporulation efficiency of mutations in the histone H4 tail.

FIG. 4D illustrates the location and sporulation efficiency phenotype of mutations in the histone 114 tail (SEQ ID NO:6).

FIG. 4E illustrates the location and sporulation efficiency phenotype of mutations in the histone H3 tail (SEQ ID NO:7).

FIG. 7E illustrates the results of an immunofluorescence experiment consistent with the results depicted in FIG. 7D.

DETAILED DESCRIPTION

Figure 1A:
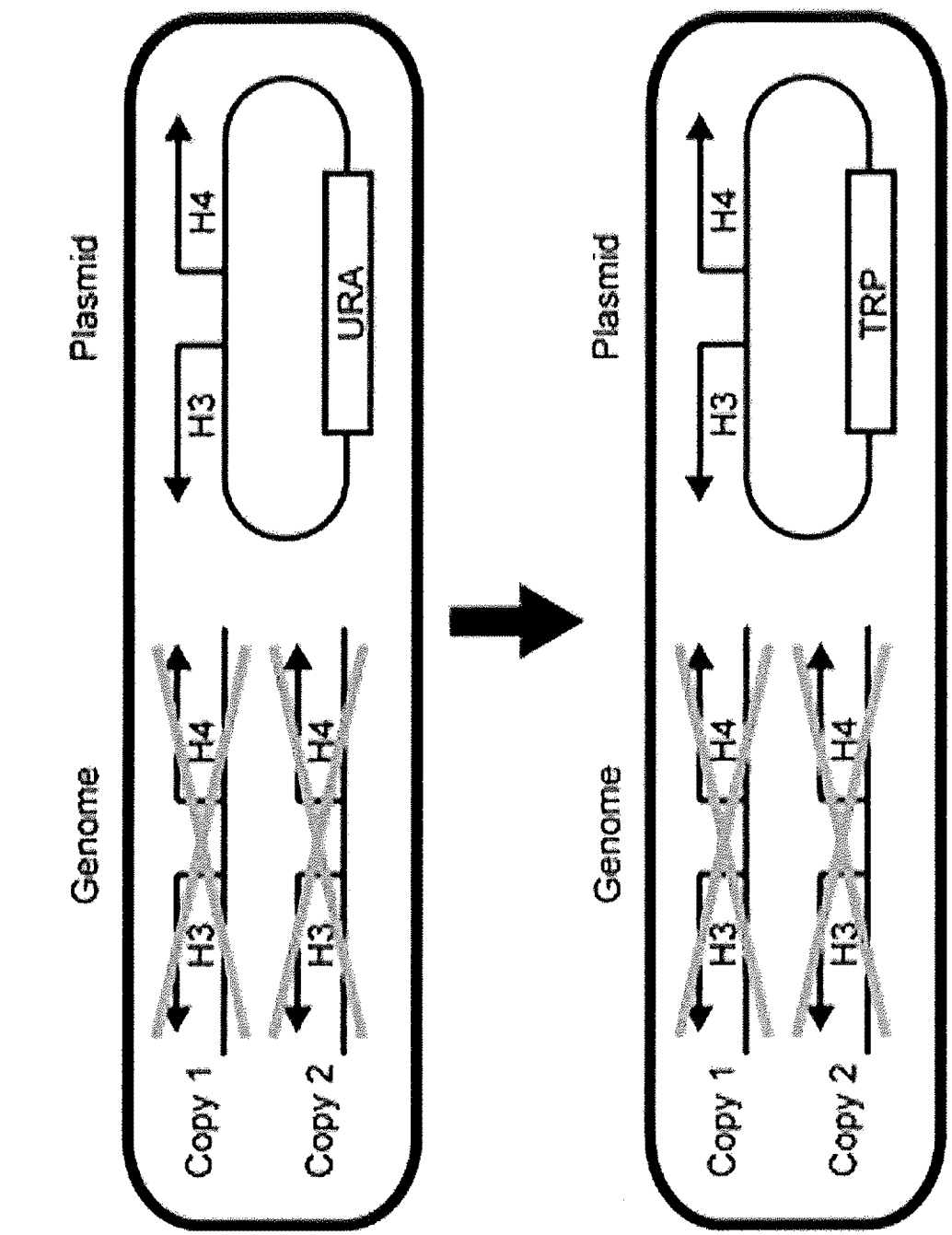
FIG. 1A illustrates a schematic representation of the histone shuffle strain. The histone shuffle strain was created in the S. cerevisiae strain SK1 background, which is well suited for the study of sporulation because the entire population synchronously and highly efficiently progresses through the sporulation process. Two genomic copies of the histones H3 and H4 were deleted. Histones H3 and H4 were then provided on a plasmid that can be shuffled for one or more different plasmids, allowing for the introduction of mutant libraries of histone H3 and H4. The wild-type histone plasmid contains a URA3 marker that can be counter-selected so that histones H3 and H4 are only expressed from the mutant TRP1 marker-containing plasmid.

The present invention relates generally to diagnostic methods and markers, prognostic methods and markers, and therapy evaluators for the study of gametogenesis, including spermatogenesis and oogenesis, and diseases or conditions associated with gametogenesis and/or fertility. The invention also relates generally to compositions and methods useful for the analysis of epigenetic control of yeast sporulation. The invention further relates to compositions and methods useful for the analysis of epigenetic control of higher-eukaryotic gametogenesis. More specifically, the invention relates to compositions and methods useful in the discovery and analyses of the epigenetic commonalities between the processes of yeast sporulation and higher-eukaryotic gametogenesis. The invention further relates to diagnostic and therapeutic compositions and methods useful in diagnosis and treating infertility.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "expression" as used herein is defined as the transcription and/or translation of a particular nucleotide sequence.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length. As used herein, the term "fragment," as applied to a nucleic acid, can ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters.

"Homologous, homology" or "identical, identity" as used herein, refer to comparisons among amino acid and nucleic acid sequences. When referring to nucleic acid molecules, "homology," "identity," or "percent identical" refers to the percent of the nucleotides of the subject nucleic acid sequence that have been matched to identical nucleotides by a sequence analysis program. Homology can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignment assessments can be obtained through the use of any standard alignment software.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell or a test tube.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. The term encompasses nucleic acids containing known analogs of natural nucleotides that have similar binding properties as the reference nucleic acid and are metabolized in a manner similar to naturally occurring nucleotides. A nucleic acid sequence can also encompass conservatively modified variants thereof (e.g., degenerate codon substitutions) and complementary sequences, as well as the sequence explicitly indicated. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "peptide" typically refers to short polypeptides.

As used herein, the term "pharmaceutically-acceptable carrier" means a chemical composition with which an appropriate delivery vehicle and nucleic acid, drug, or compound can be combined and which, following the combination, can be used to administer the appropriate delivery vehicle and nucleic acid, drug, or compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

A "polynucleotide" means a single strand or parallel and anti-parallel strands of a nucleic acid. Thus, a polynucleotide may be either a single-stranded or a double-stranded nucleic acid.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but can be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

The terms "promoter," "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, "phenotypically distinct" is used to describe organisms, cells or components thereof, which can be distinguished by one or more characteristics, observable and/or detectable by current technologies. Each of such characteristics may also be defined as a parameter contributing to the definition of the phenotype. Wherein a phenotype is defined by one or more parameters an organism that does not conform to one or more of the parameters shall be defined to be distinct or distinguishable from organisms of the the phenotype.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning and amplification technology, and the like, and by synthetic means. An "oligonucleotide" as used herein refers to a short polynucleotide, typically less than 100 bases in length.

A "prophylactic" treatment is a treatment administered to a subject who does not exhibit signs of a disease or exhibits only early signs of the disease for the purpose of decreasing the risk of developing pathology associated with the disease.

The term "protein" typically refers to large polypeptides.

"Slow release," as used herein, refers to delivery of a nucleic acid, drug, or molecule to a cell, tissue, or organ, wherein the nucleic acid, drug, or molecule is not all readily available because some remains bound to the delivery vehicle or to an anionic molecule and is slowly released for availability over a period of time. The period of time should be at least 10% longer than availability that is not slow release, preferably at least 25% longer, more preferably at least 35% longer and even more preferably at least 50% longer. Such a drug or molecule can include a prodrug or steroid prodrug.

"Synthetic peptides or polypeptides" mean a non-naturally occurring peptide or polypeptide. Synthetic peptides or polypeptides can be synthesized, for example, using an automated polypeptide synthesizer. Those of skill in the art know of various solid phase peptide synthesis methods.

A "therapeutic" treatment is a treatment administered to a subject who exhibits signs of pathology, for the purpose of diminishing or eliminating those signs.

The terms "marker" and "epigenetic marker" are used interchangeably herein to refer to a distinguishing or characteristic substance that may be found in a biological material.

The substance may, for example, be a protein, an enzyme, an RNA molecule or a DNA molecule. Non-limiting examples of such a substance include a kinase, a methylase, and an acetylase. The terms also refer to a specific characteristic of the substance, such as, but not limited to, a specific phosphorylation, methylation, or acetylation event or pattern, making the substance distinguishable from otherwise identical substances. The terms further refer to a specific modification, event or step occurring in a signaling pathway or signaling cascade, such as, but not limited to, the deposition or removal of a specific phosphate, methyl, or acetyl group.

A cell has been "transformed," "transduced" or "transfected" by exogenous or heterologous DNA when such DNA has been introduced inside the cell. The introduced DNA may or may not be integrated (covalently linked) into the genome of the cell. In prokaryotes, yeast, and mammalian cells for example, the introduced DNA may be maintained on an episomal element such as a plasmid. With respect to eukaryotic cells, a stably transformed or transduced cell is one in which the introduced DNA has become integrated into a chromosome so that it is inherited by daughter cells through chromosome replication. This stability is demonstrated by the ability of the eukaryotic cell to establish cell lines or clones comprised of a population of daughter cells containing the introduced DNA. A "clone" is a population of cells derived from a single cell or common ancestor by mitosis. A "cell line" is a clone of a primary cell that is capable of stable growth in vitro for many generations.

The term to "treat," as used herein, means reducing the frequency with which symptoms are experienced by a patient or subject or administering an agent or compound to reduce the frequency with which symptoms are experienced.

As used herein, "treating a disease or disorder" means reducing the frequency with which a symptom of the disease or disorder is experienced by a patient. Disease and disorder are used interchangeably herein.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector," as used herein, refers to either a delivery vehicle as described herein or to a vector such as an expression vector.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5,3, and 6. This applies regardless of the breadth of the range.

Yeast Libraries

In one embodiment, the invention provides a yeast library useful for the identification of epigenetic markers involved in yeast sporulation and/or mammalian gametogenesis. In various embodiments, each member of the yeast library has histone H3 and histone H4 deleted from its genome. Instead, the wild-type histone sequence of one of the two histones H3 and H4 is expressed from a plasmid and the other of the two wild-type histone sequences that is not expressed from a plasmid is substituted with a mutant histone sequence expressed from a plasmid. In some embodiments, the mutant histone sequence has one of its wild-type amino acid residues substituted with another amino acid. In preferred embodiments, the wild-type amino acid is substituted with an alanine. In preferred embodiments, the yeast library is constructed so that each member of the yeast library has only a single mutation, but altogether, every amino acid position mutation in H3 and H4 is present at least one time in the library. In some embodiments, the yeast is an S. cerevisiae strain. In preferred embodiments the S. cerevisiae strain is SK1.

In another embodiment, the invention provides a yeast library useful for the identification of epigenetic markers involved in yeast sporulation and/or mammalian gametogenesis. In various embodiments, each member of the yeast library has histone H2A and histone H2B deleted from its genome. Instead, the wild-type histone sequence of one of the two histones H2A and H2B is expressed from a plasmid and the other of the two wild-type histone sequences that is not expressed from a plasmid is substituted with a mutant histone sequence expressed from a plasmid. In some embodiments, the mutant histone sequence has one of its wild-type amino acid residues substituted with another amino acid. In preferred embodiments, the wild-type amino acid is substituted with an alanine. In preferred embodiments, the yeast library is constructed so that each member of the yeast library has only a single mutation, but altogether, every amino acid position mutation in H2A and H2B is present at least one time in the library. In some embodiments, the yeast is an S. cerevisiae strain. In preferred embodiments the S. cerevisiae strain is SK1.

In a further embodiment, the invention provides a yeast library useful for the identification of epigenetic markers involved in yeast sporulation and/or mammalian gametogenesis. In various embodiments, each member of the yeast library has histones H2A, H2B, H3 and H4 deleted from its genome. Instead, the wild-type histone sequence of three of the four histones H2A, H2B, H3 and H4 is expressed from a plasmid and the other of the four wild-type histone sequences that is not expressed from a plasmid is substituted with a mutant histone sequence expressed from a plasmid. In some embodiments, the mutant histone sequence has one of its wild-type amino acid residues substituted with another amino acid, In preferred embodiments, the wild-type amino acid is substituted with an alanine. In preferred embodiments, the yeast library is constructed so that each member of the yeast library has only a single mutation, but altogether, every amino acid position mutation in H2A, H2B, H3 and H4 is present at least one time in the library. In some embodiments, the yeast is an S. cerevisiae strain. In preferred embodiments the S. cerevisiae strain is SK1.

Screening Methods and Markers

In some embodiments, the invention provides screening methods for identifying an epigenetic marker associated with yeast sporulation, or useful in the diagnosis of infertility or a disorder associated with gametogenesis. Generally, the screening methods of the invention employ the use of yeast libraries of mutant histones, as described elsewhere herein. In various embodiments, the screening methods involve creation of such a yeast library of mutant histones, induction of sporulation, assessment of the sporulation efficiency of individual mutants, identification of particular amino acid residues of mutants demonstrating diminished sporulation efficiency, evaluation of the epigenetic modifications at these amino acid residues, evaluation of the epigenetic modifications at the same amino acid position of a mammalian histone, whereby when the epigenetic modification state of the yeast histone is the same as the mammalian histone, an epigenetic marker for the diagnosis of infertility or a disorder associated with gametogenesis is identified. In some embodiments, gametogenesis refers to spermatogenesis, while in other embodiments, gametogenesis refers to oogenesis. In various embodiments, the epigenetic marker is at least one of methylation, acetylation, phosphorylation, or any of the aforementioned modifications, or the lack thereof, of a particular histone amino acid residue. In preferred embodiments, the epigenetic marker of the invention is phosphorylated or unphosphorylated H3T11. In other embodiments, the epigenetic marker is a histone amino acid residue that is phosphorylated by Mek1 or a homologue.

In another embodiment, the invention is an epigenetic marker that is identified using the yeast libraries or the screening methods elsewhere described herein. In some embodiments, the epigenetic marker is restricted to meiosis. In preferred embodiments, the presence of the epigenetic marker during yeast sporulation correlates with the presence of the epigenetic marker during mammalian gametogenesis. In some embodiments, gametogenesis refers to spermatogenesis, while in other embodiments, gametogenesis refers to oogenesis. In various embodiments, the epigenetic marker is at least one of methylation, acetylation, or phosphorylation of a particular histone amino acid residue, or the lack thereof. In preferred embodiments, the epigenetic marker of the invention is phosphorylated or unphosphorylated H3T11. In other embodiments, the epigenetic marker is a histone amino acid residue that is phosphorylated by Mek1 or a homologue.

The skilled artisan will understand that the term epigenetic marker is used herein in a non-limiting way to include not only a specific characteristic of the substance, such as, but not limited to, a specific phosphorylation, methylation, or acetylation event or pattern, but also includes substances that may be found in a biological material, such as a protein or an enzyme, as well as the signaling cascades and signaling pathways within which such substances participate.

Diagnostic and Evaluative Methods

In additional embodiments, the invention provides methods for using the epigenetic marker identified using the yeast libraries and/or screening methods elsewhere described herein as a diagnostic marker of infertility or a disorder associated with gametogenesis. In various embodiments, the altered relative timing of or the presence or absence of, a particular normal or abnormal epigenetic marker is used herein as a diagnostic marker of infertility or a disorder associated with gametogenesis. In some embodiments, gametogenesis refers to spermatogenesis, while in other embodiments, gametogenesis refers to oogenesis. In some embodiments, the method comprises the steps of obtaining a biological sample from an individual, assessing the biological sample for the presence of a particular epigenetic marker, whereby when the epigenetic marker is present in the biological sample, the individual is diagnosed with infertility or a disorder associated with gametogenesis. In some embodiments, the individual is a mammal and in preferred embodiments, the mammal is human. In other embodiments, the method comprises the steps of obtaining a biological sample from an individual, assessing the biological sample for the presence of a particular epigenetic marker, whereby when the epigenetic marker is absent in the biological sample, the individual is diagnosed with infertility or a disorder associated with gametogenesis. In some embodiments, the individual is a mammal and in preferred embodiments, the mammal is human.

In still further embodiments, the invention provides methods of monitoring a particular epigenetic marker to evaluate the progress of a therapeutic treatment of modulating fertility or a disorder associated with gametogenesis. In some embodiments, the individual is a mammal and in preferred embodiments, the mammal is human.

The invention also provides methods for screening an individual to determine if the individual is at increased risk of infertility or a disorder associated with gametogenesis. Individuals found to be at increased risk can be given appropriate therapy and monitored using the methods of the invention.

In the various methods of diagnosing, evaluating and screening of individuals described herein, the epigenetic marker is, in some embodiments, at least one of methylation, acetylation, or phosphorylation of a particular histone amino acid residue, or the lack thereof. In preferred embodiments, the epigenetic marker of the invention is phosphorylated or unphosphorylated H3T11. In other embodiments, the epigenetic marker is a histone amino acid residue that is phosphorylated by Mek1 or a homologue. As elsewhere described herein, the skilled artisan will understand that the term epigenetic marker is used herein in a non-limiting way to include not only a specific characteristic of the substance, such as, but not limited to, a specific phosphorylation, methylation, or acetylation event or pattern, but also includes substances that may be found in a biological material, such as a protein or an enzyme, as well as the signaling cascades and signaling pathways within which such substances participate.

Kits

The invention also provides kits for the identification of epigenetic markers associated with gametogenesis or fertility as elsewhere described herein. In one embodiment, the kit includes a yeast library, as elsewhere described herein, and instructions for its use. The instructions will generally include information about the use of the compositions in the kit for the identification of epigenetic markers as associated with gametogenesis or fertility. The instructions may be printed directly on a container inside the kit (when present), or as a label applied to the container, or as a separate sheet, pamphlet, card, or folder supplied in or with the container.

The invention also provides kits for the diagnosis of a disease or disorder (or symptoms) thereof associated with gametogenesis or fertility. In one embodiment, the kit includes the materials needed for the detection of a particular epigenetic marker in biological sample of an individual and instructions. The instructions will generally include information about the use of the compositions in the kit for the diagnosis of a disease or disorder or symptoms thereof associated with gametogenesis or fertility. The instructions may be printed directly on a container inside the kit (when present), or as a label applied to the container, or as a separate sheet, pamphlet, card, or folder supplied in or with the container.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Creation of Mutant Histone Libraries

A library of alanine mutants at all residues of histones H3 and H4, except at the naturally occurring alanine residues in yeast S. cerevisiae strain SK1, was created essentially as previously described, with some modification (see Nakanishi et al., 2008, Nature Structural & Molecular Biology 15:881-88). Plasmids containing alanine point mutations within the histone genes were generated by site-directed mutagenesis. Each plasmid was then sequenced for confirmation. The entire collection of the histone alanine mutant library in S. cerevisiae was generated by transforming the plasmids into the yeast histone shuffle S. cerevisiae strain SKI. Strain selection for transformants was conducted, followed by a second single-colony selection on 5-fluoroorotic acid (5-FOA) to remove wild-type histone plasmids containing the URA3 gene (See FIG. 1A). Individual strains in the final yeast histone mutation library were sequenced for confirmation of the mutation and to determine the absence of the corresponding wild-type histone copy. The skilled artisan will understand that although FIG. 1A illustrates the expression of both H3 and H4 from the same plasmid, in various embodiments the invention encompasses the expression of H3 and H4 from either the same plasmid or from different plasmids.

A library of alanine mutants at all residues of histones H2A and H2B, except at the naturally occurring alanine residues in yeast S. cerevisiae strain SK1, is created essentially as previously described, with some modification (see Nakanishi et al., 2008, Nature Structural & Molecular Biology 15:881-88). Plasmids containing alanine point mutations within the histone genes were generated by site-directed mutagenesis. Each plasmid was then sequenced for confirmation. The entire collection of the histone alanine mutant library in S. cerevisiae is generated by transforming the plasmids into the yeast histone shuffle S. cerevisiae strain SK1. Strain selection for transformants is conducted, followed by a second single-colony selection on 5-fluoroorotic acid (5-FOA) to remove wild-type histone plasmids containing the URA3 gene. Individual strains in the final yeast histone mutation library are sequenced for confirmation of the mutation and to determine the absence of the corresponding wild-type histone copy. The skilled artisan will understand that in various embodiments the invention encompasses the expression of H2A and H2B from either the same plasmid or from different plasmids.

A library of alanine mutants at all residues of histones H2A, H2B, H3 and H4, except at naturally occurring alanine residues in yeast S. cerevisiae strain, is created essentially as previously described, with some modification (see Nakanishi et al., 2008, Nature Structural & Molecular Biology 15:881-88), and as elsewhere described herein. The skilled artisan will understand that in various embodiments the invention encompasses the expression of H2A, H2B, H3 and H4 from either the same plasmid, or from two or three or four different plasmids.

Example 2

Screen of Mutants for Sporulation Efficiency

Figure 1B:
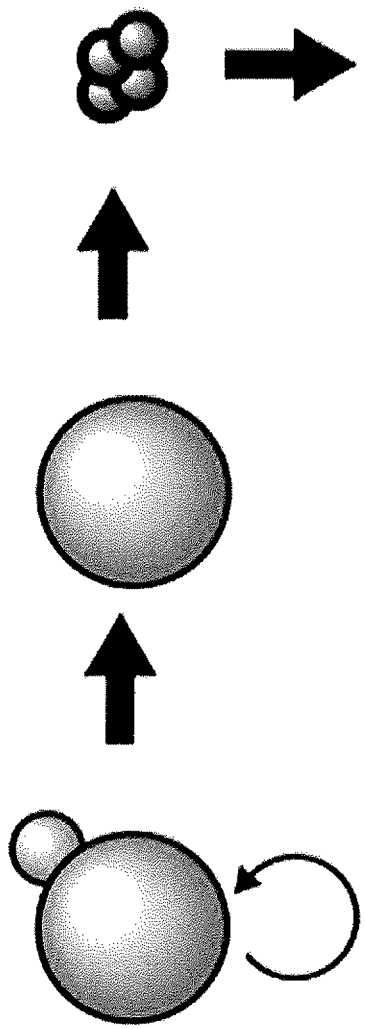
FIG. 1B illustrates a schematic of the screening process.

FIG. 1B illustrates a schematic of the screening process. Mutations inducing growth defects were excluded from the library. The phenotype of all other mutants was assessed during sporulation. Sporulation was induced as follows. Each mutant was grown individually in 5 mL rich media (i.e., YPD). The mutant was transferred to acetate media (i.e., YPA) for about 15-20 hours until an OD of 0.8 was reached. Sporulation was induced in 2% potassium acetate for about 24 hours at an OD of 2. Sporulation efficiency for each mutant was determined by counting the fraction of tetrads compared to the total amount of cells.

Figure 1C:
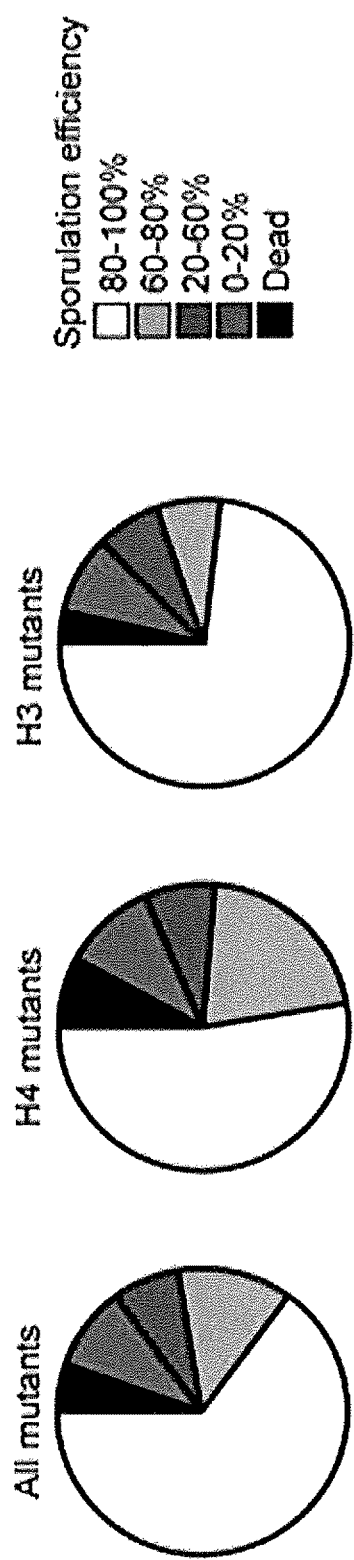
FIG. 1C illustrates the results of a sporulation efficiency assay.
Figure 1D:
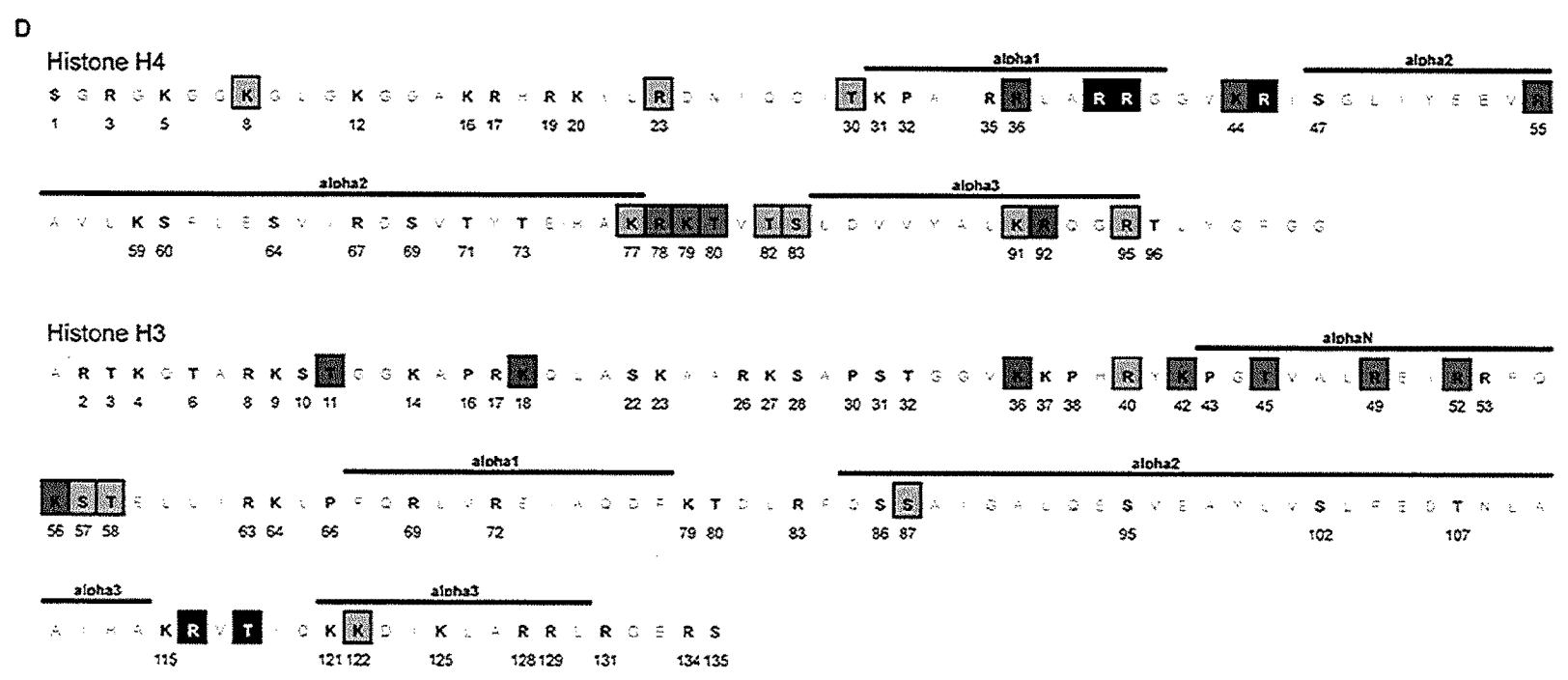
Figure 2:
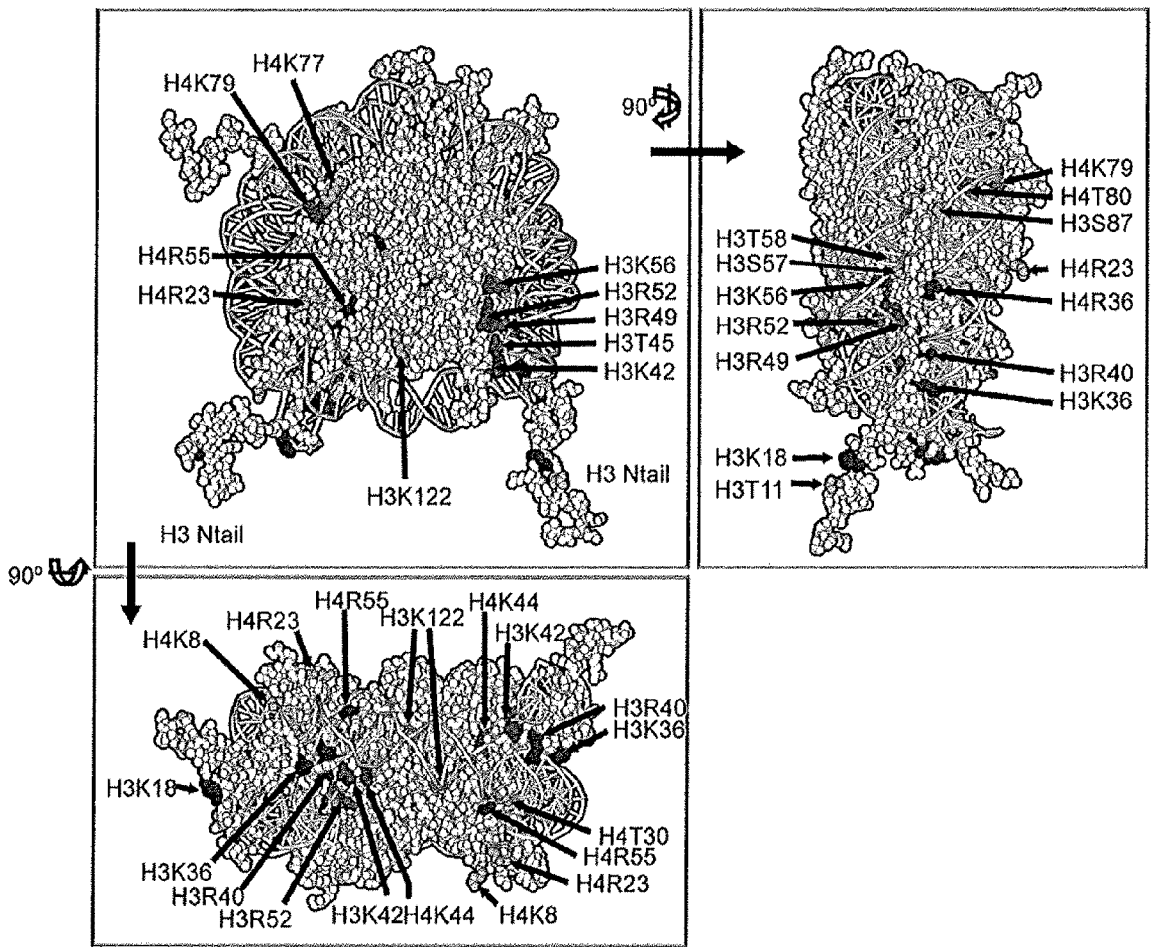
FIG. 2 illustrates the three-dimensional location of the mutations depicted in FIG. 1D.

FIG. 1C shows pie charts depicting the fraction of mutants that lead to a sporulation efficiency of 0-20%, 20-60%, 60-80%, or 80-100%, as well as the fraction that lead to death, for the H3 mutant library, the H4 mutant library, and the H3 and H4 mutant libraries combined. FIG. 1D illustrates the sporulation efficiency associated with each mutation within the library, while FIG. 2 illustrates the three-dimensional location of the mutations depicted in FIG. 1D.

Figure 3:
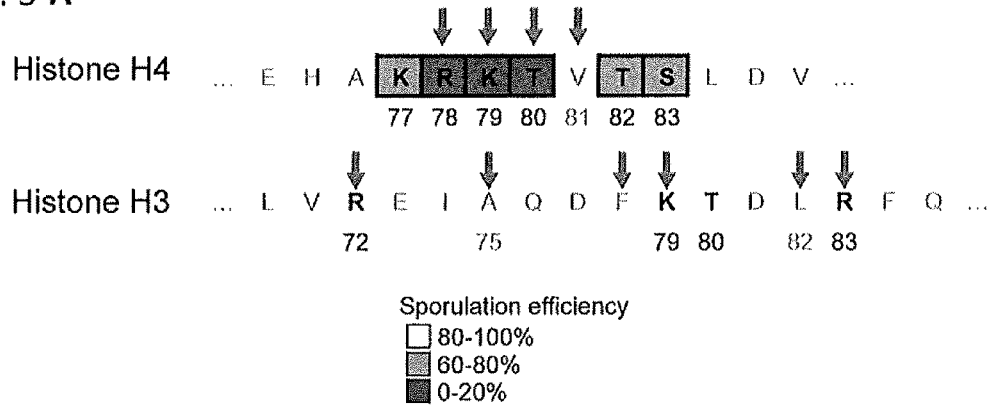
FIG. 3A illustrates the location and sporulation efficiency phenotype of mutations in the LRS patch, one of two patches identified as important for sporulation (SEQ ID NO:3, top, and SEQ ID NO:4, bottom). The arrows indicate mutations in the LRS patch that were identified in previous studies, although previous studies did not identify these mutations as important for sporulation. As disclosed herein, only H4 LRS patch mutants were observed to be sporulation deficient.
FIG. 3B illustrates the three-dimensional location of the mutations in the LRS patch depicted in FIG. 3A.
FIG. 3C illustrates the location and sporulation efficiency phenotype of mutations in the DNA entry/exit patch, one of two patches identified as important for sporulation (SEQ ID NO:5).
FIG. 3D illustrates the three-dimensional location of the mutations in the DNA entry/exit patch depicted in FIG. 3c
FIG. 3E illustrates the results of an example experiment assessing sporulation efficiency of H3K56 mutants.
Figure 3:
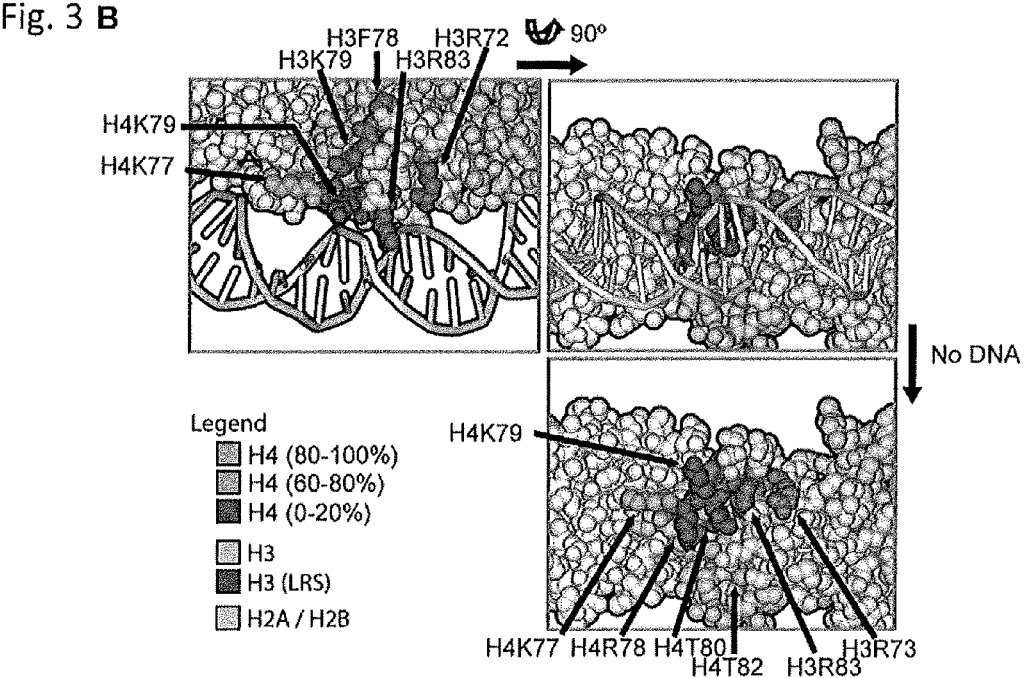
Figure 3:
Figure 3:
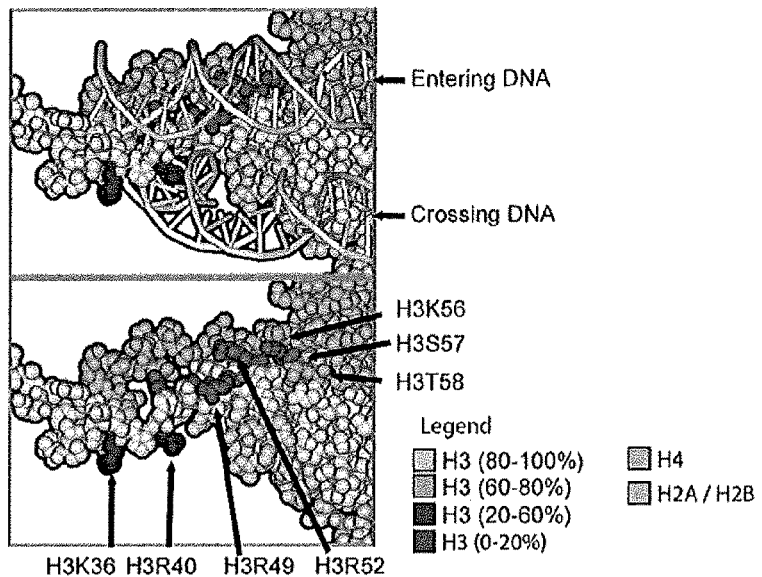
Figure 3:
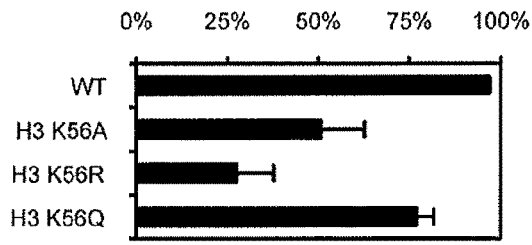
Figure 5A:
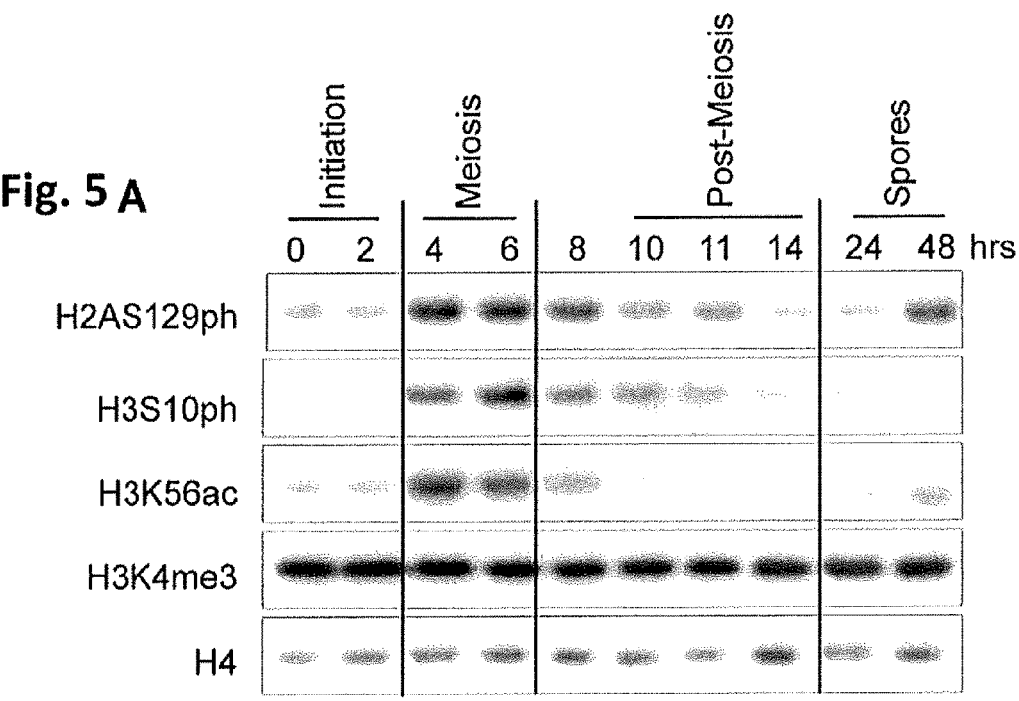
FIG. 5A illustrates the results of an example experiment assessing histone modification during sporulation.
Figure 5B:
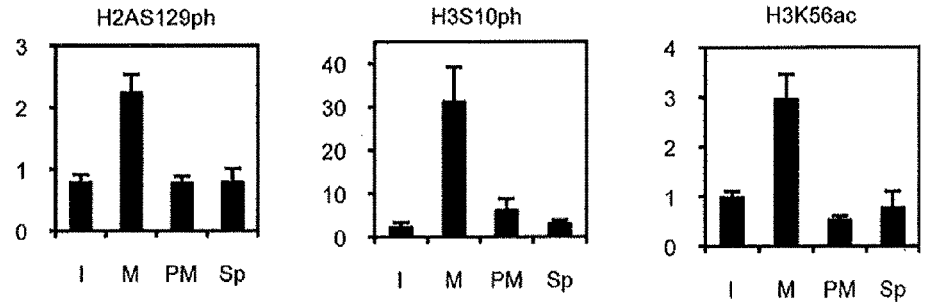
FIG. 5B illustrates the quantification of the example experiment assessing histone modification during sporulation depicted in FIG. 5A.

FIG. 3A illustrates the location and sporulation efficiency phenotype of mutations in the LRS patch, one of two patches identified as important for sporulation. The arrows indicate mutations in the LRS patch that were identified in previous studies, although the importance of these mutations for sporulation is disclosed for the first time herein. As disclosed herein, only H4 LRS patch mutants were observed to be sporulation deficient. FIG. 3B illustrates the three-dimensional location of the mutations in the LRS patch depicted in FIG. 3A.

FIG. 3C illustrates the location and sporulation efficiency phenotype of mutations in the DNA entry/exit patch, one of two patches identified as important for sporulation. The DNA entry/exit patch is the location on the nucleosome where the DNA is entering. Full integrity of this patch appears to be important for the completion of sporulation. FIG. 3D illustrates the three-dimensional location of the mutations in the DNA entry/exit patch depicted in FIG. 3C. FIG. 3E illustrates the results of an example experiment assessing sporulation efficiency of H3K56 mutants.

FIG. 4 illustrates the results of experiment assessing the effect of mutations in the histone tail on sporulation. Seventy percent of the mutants assessed in FIGS. 4A, 4B and 4C had little to no effect on sporulation efficiency. FIG. 4D illustrates the location and sporulation efficiency phenotype of each mutation in the histone H4 tail, while FIG. 4E illustrates the location and sporulation efficiency phenotype of each mutation in the histone H3 tail.

Example 3

Identification that H3T11 is Phosphorylated in Yeast

Figure 6:
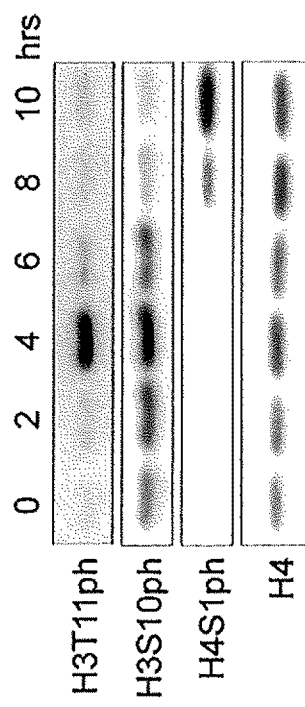
FIG. 6A illustrates the results of an example experiment assessing the sporulation efficiency of the H3S10A and H3T11A mutations.
FIG. 6B illustrates the results of an example experiment assessing the phosphorylation state of the H3S10ph, H3T11ph and H4S1ph.
FIG. 6C illustrates the quantification of the example experiment assessing phosphorylation state depicted in FIG. 6B.
FIG. 6D illustrates the results of an example experiment assessing kinase activity at H3S10 and H3T11.
FIG. 6E illustrates the H3T11ph pattern during mouse spermatogenesis.
Figure 6A:
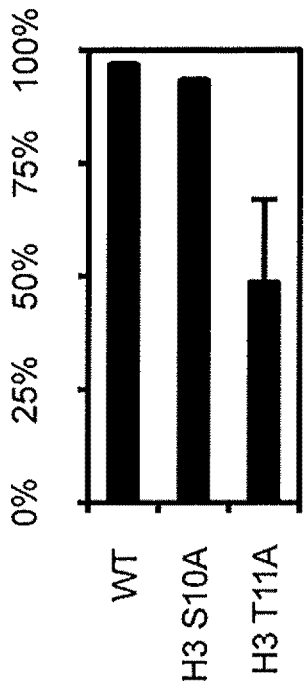
Figure 6C:
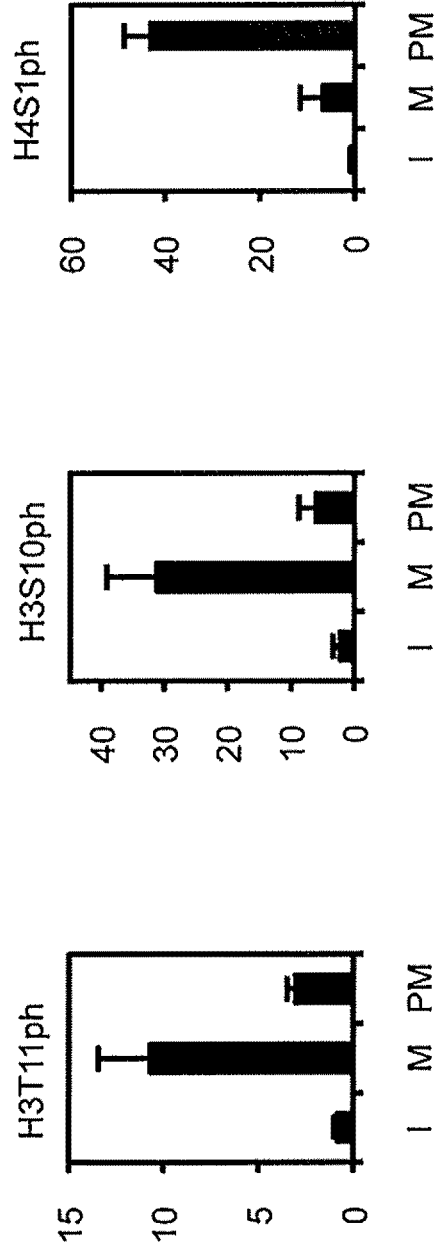

FIG. 6A illustrates the results of an example experiment assessing the sporulation efficiency of the H3S10A and H3T11A mutants. H3T11A is sporulation deficient, while H3S10A is not. FIG. 6B illustrates the results of an example experiment assessing the phosphorylation state of the H3S10, H3T11 and H4S1 at 0, 2, 4, 6, 8 and 10 hours following induction of sporulation. As disclosed herein for the first time, H3T11 is phosphorylated in yeast during sporulation and its phosphorylation is restricted to meiosis. FIG. 6C illustrates a quantification of the intensity of the signals on the blot depicted in FIG. 6B during Initiation (I—0 hour and 2 hours after induction of sporulation), Meiosis (M—4 hours and 6 hours after induction of sporulation) and Post-Meiosis (PM—10-14 hours after induction of sporulation).

Example 4

Identification of the H3T11ph Kinase

FIG. 6D illustrates the results of an example experiment assessing kinase activity at H3S10 and H3T11. Ip11 is the H3S10ph kinase. Deletion of Ip11 during sporulation prevents H3S10ph deposition, but deletion of Ip11 has no effect on H3T11ph. In contrast, deletion of Mek1 prevents H3T11ph deposition, but has no effect on H3S10ph.

Example 5

H3T11ph Pattern During Mouse Spermatogenesis

FIG. 6F illustrates the H3T11ph pattern during mouse spermatogenesis. Similar to the results depicted in FIGS. 6B and 6C, the phosphorylation of H3T11 is restricted to meiosis.

Example 6

Analysis of Histone Modifications During the Post-meiotic Phase of Sporulation

Figure 7A:
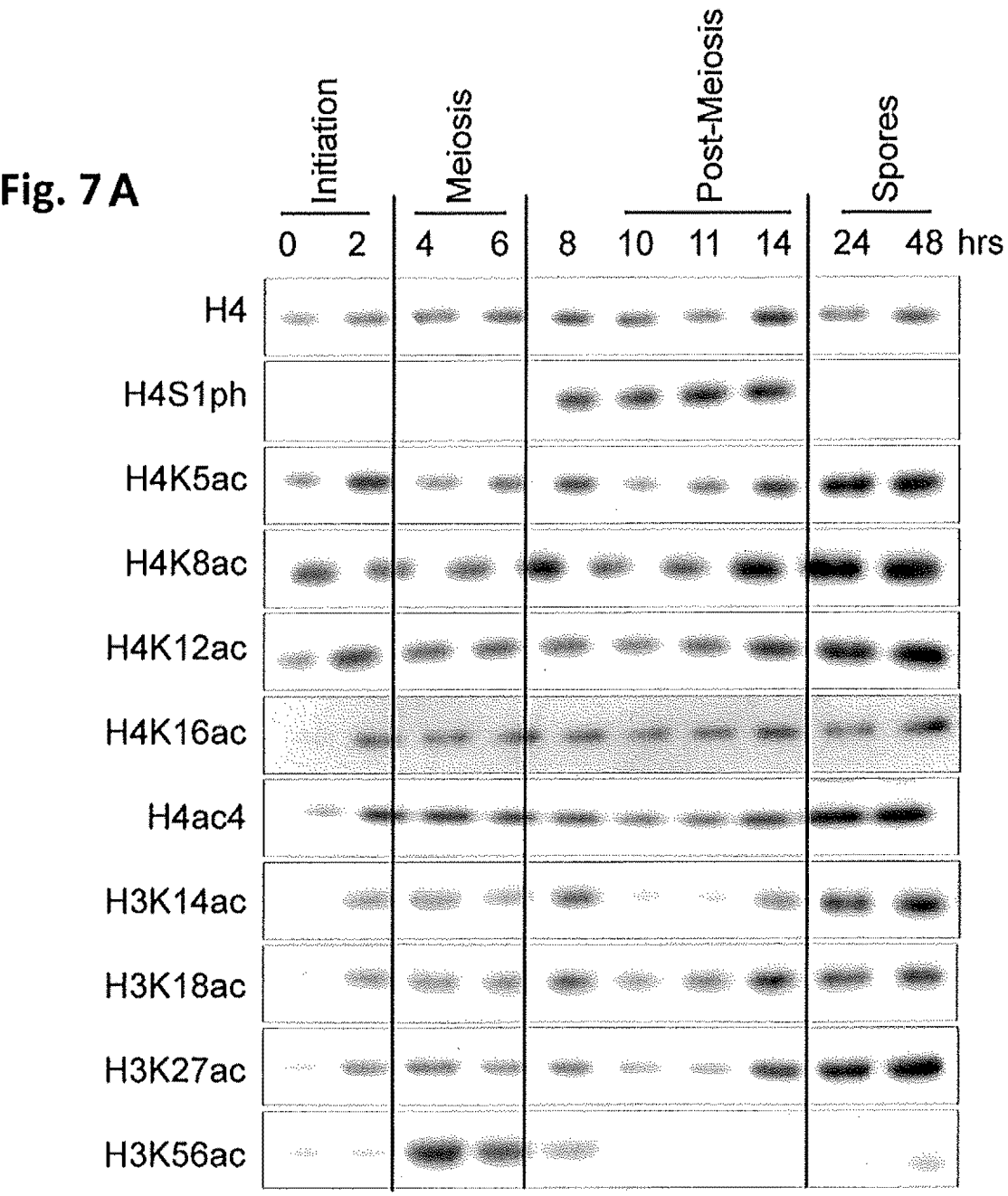
FIG. 7A illustrates the results of an example experiment assessing histone H3 and H4 modification during sporulation.
Figure 7B:
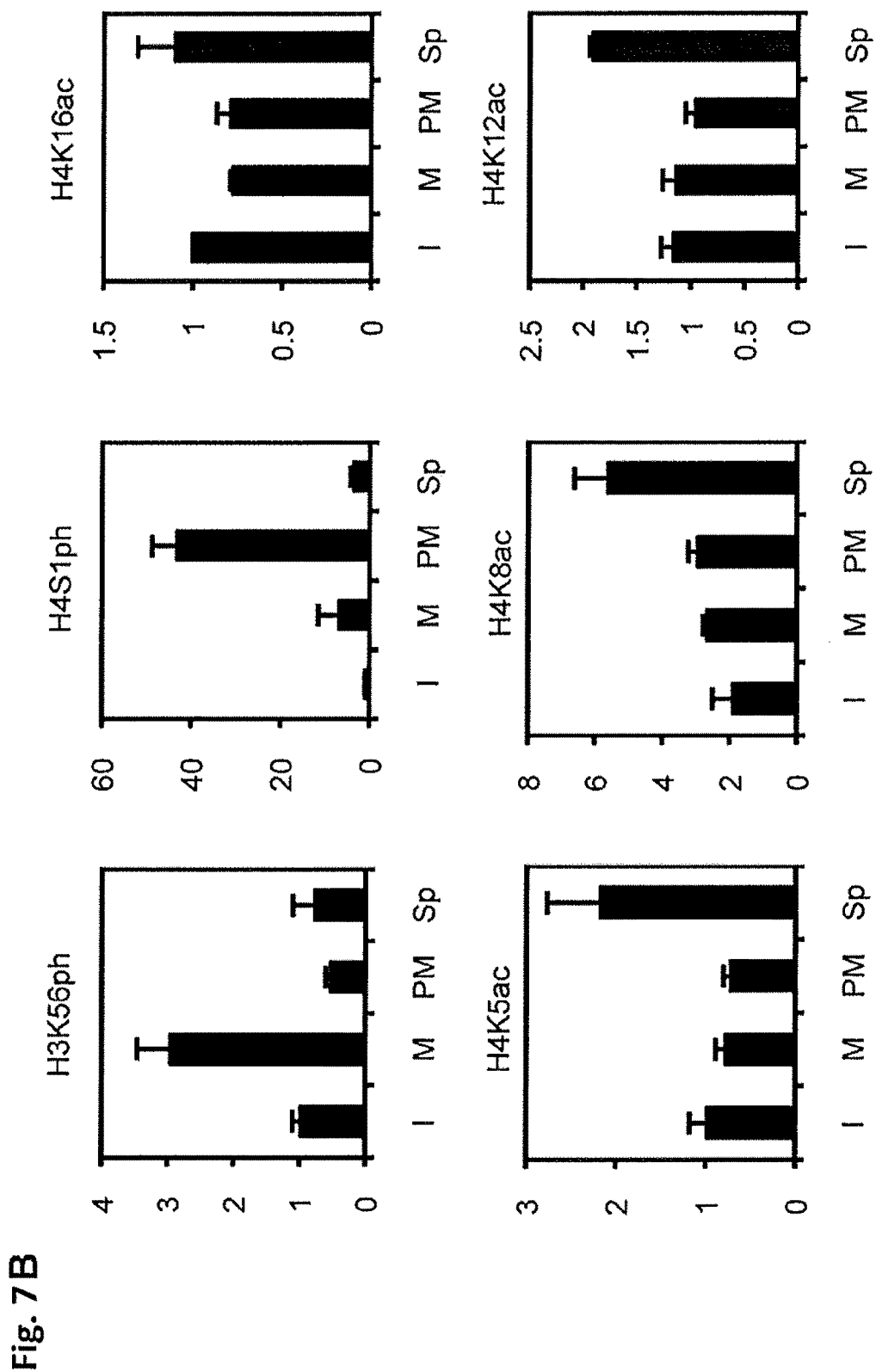
FIG. 7B illustrates the quantification of the example experiment assessing histone H3 and H4 modification depicted in FIG. 7A.

FIG. 7A illustrates the results of an example experiment assessing histone H3 and H4 modification during sporulation. As disclosed herein for the first time, H4S1ph is diminished in mature spores, while H4 is hyperacetylated at H4K5, H4K8 and H4K12. FIG. 7B illustrates the quantification of the example experiment assessing histone H3 and H4 modification depicted in FIG. 7A.

Figure 7C:
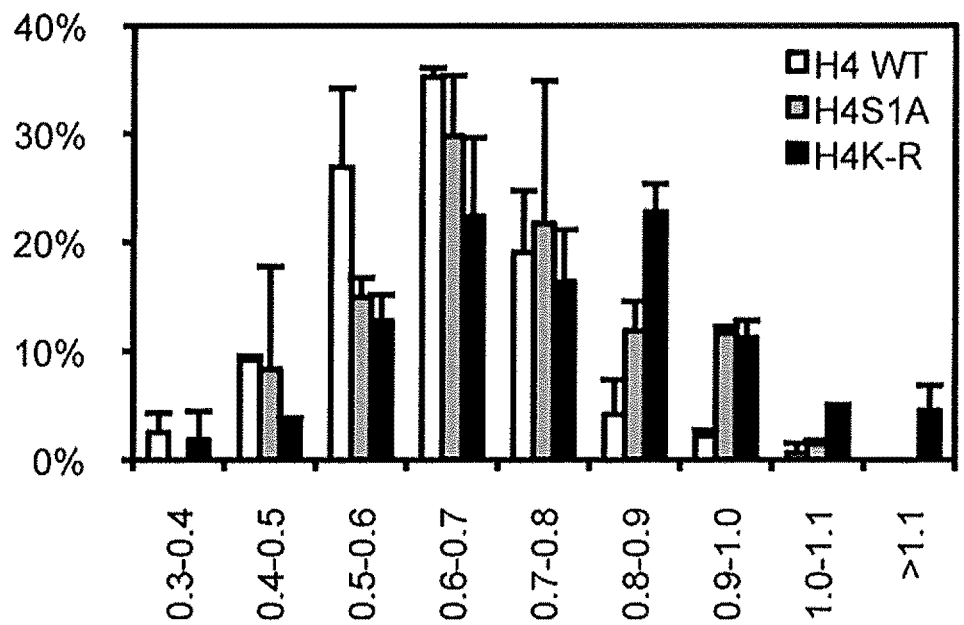
FIG. 7C illustrates the results of an example experiment demonstrating that preventing histone H4 acetylation leads to a defect in nuclear compaction in mature spores.
Figure 7D:
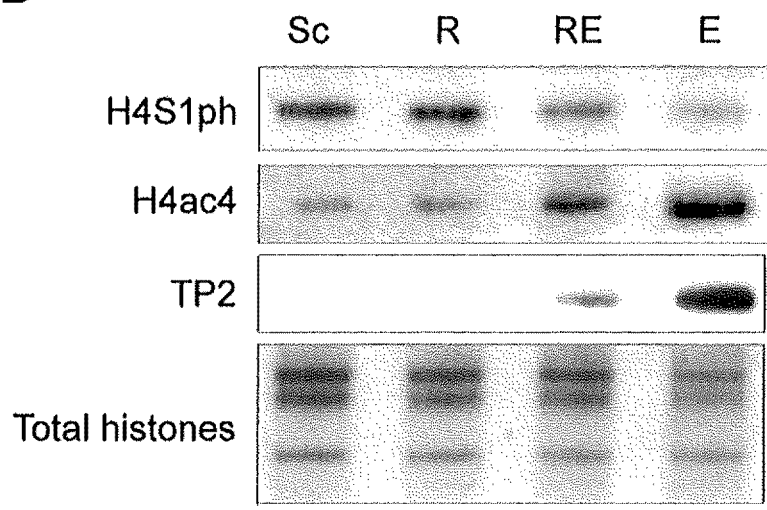
FIG. 7D illustrates the results of an example experiment assessing H4S1ph and H4 acetylation state during spermatogenesis. The same trends occur in higher eukaryotes' gametogenesis. Sc=spermatocytes; R=Round spermatids; RE=mix of round and elongating spermatids; E=elongated spermatids.

FIG. 7C illustrates the results of an example experiment demonstrating that preventing histone H4 acetylation leads to a defect in nuclear compaction in mature spores. FIG. 7D illustrates the results of an example experiment assessing H4S1ph and H4 acetylation state during spermatogenesis, indicating that the same trends occur in gametogenesis in higher eukaryotes. (Sc=spermatocytes; R=Round spermatids; RE=mix of round and elongating spermatids; E=elongated spermatids.). FIG. 7E illustrates the results of an immunofluorescence experiment consistent with the results depicted in FIG. 7D.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising an *S. cerevisiae* strain SK1 yeast library, wherein each member of the yeast library has histone H3 and histone H4 deleted from its genome; and wherein the wild-type histone sequence of one of said two histones H3 and H4 is expressed from a plasmid; and wherein the remaining one of said two wild-type histone sequences that is not expressed from a plasmid is substituted with a mutant histone sequence expressed from a plasmid; and wherein said mutant histone sequence has one of its wild-type amino acid residues substituted with alanine; and wherein each member of said yeast library has only a single mutation; and wherein each amino acid position mutation in H3 and H4 is present at least one time in said library.

2. A composition comprising an *S. cerevisiae* strain SK1 yeast library, wherein each member of said yeast library has histone H2A and histone H2B deleted from its genome; and wherein the wild-type histone sequence of one of said two histones H2A and H2B is expressed from a plasmid; and wherein the remaining one of said two wild-type histone sequences that is not expressed from a plasmid is substituted with a mutant histone sequence expressed from a plasmid; and wherein said mutant histone sequence has one of its wild-type amino acid residues substituted with alanine; and wherein each member of said yeast library has only a single mutation; and wherein each amino acid position mutation in H2A and H2B is present at least one time in said library.

3. A composition comprising an *S. cerevisiae* strain SK1 yeast library, wherein each member of said yeast library has histone H2A, histone H2B, histone H3 and histone H4 deleted from its genome; and wherein the wild-type histone sequence of three of said four histones H2A, H2B, H3, and H4 is expressed from a plasmid; and wherein the remaining one of said four wild-type histone sequences that is not expressed from a plasmid is substituted with a mutant histone sequence expressed from a plasmid; and wherein said mutant historic sequence has one of its amino acid residues substituted with alanine; and wherein each member of said yeast library has only a single mutation; and wherein each amino acid position mutation in H2A, H2B, H3 and H4 is present at least one time in said library.

4. A method of identifying an epigenetic marker for diagnosis of infertility or a disorder associated with gametogenesis, said method comprising the steps of:
 (a) creating an *S. cerevisiae* strain SK1 yeast library of mutant histones,
 (b) inducing sporulation,
 (c) assessing efficiency of said sporulation in individual mutants,
 (d) identifying particular amino acid positions of said mutants with diminished efficiency of said sporulation,
 (e) evaluating epigenetic modifications at said amino acid positions, and,
 (f) evaluating epigenetic modifications at the same amino acid position of a mammalian histone,
whereby, when the epigenetic modification state of said yeast histone is the same as said mammalian histone, said epigenetic marker for said diagnosis of said infertility or said disorder associated with gametogenesis is identified.

5. The method of claim 4, wherein each member of the yeast library has historic H3 and histone H4 deleted from its genome; and wherein the wild-type histone sequence of one of said two histones H3 and H4 is expressed from a plasmid; and wherein the remaining one of said two wild-type histone sequences that is not expressed from a plasmid is substituted with a mutant histone sequence expressed from a plasmid; and wherein said mutant histone sequence has one of its wild-type amino acid residues substituted with alanine; and wherein each member of said yeast library has only a single mutation; and wherein each amino acid position mutation in H3 and H4 is present at least one time in said library.

6. The method of claim 4, wherein each member of said yeast library has histone H2A and histone H2B deleted from its genome; and wherein the wild-type histone sequence of one of said two histones H2A and H2B is expressed from a plasmid; and wherein the remaining one of said two wild-type histone sequences that is not expressed from a plasmid is substituted with a mutant histone sequence expressed from a plasmid; and wherein said mutant histone sequence has one of its wild-type amino acid residues substituted with alanine; and wherein each member of said yeast library has only a single mutation; and wherein each amino acid position mutation in H2A and H2B is present at least one time in said library.

7. The method of claim 4, wherein each member of said yeast library has histone H2A, histone H2B, histone H3 and histone H4 deleted from its genome; and wherein the wild-type histone sequence of three of said four histones H2A, H2B, H3, and H4 is expressed from a plasmid; and wherein the remaining one of said four wild-type histone sequences that is not expressed from a plasmid is substituted with a mutant histone sequence expressed from a plasmid; and wherein said mutant histone sequence has one of its amino acid residues substituted with alanine; and wherein each member of said yeast library has only a single mutation; and wherein each amino acid position mutation in H2A, H2B, H3 and H4 is present at least one time in said library.

8. The method of claim 4, wherein said marker is restricted to meiosis.

9. The method of claim 4, wherein the presence of said marker during said yeast sporulation correlates with the presence of said marker during said gametogenesis.

10. The method of claim 4, wherein said marker is at least one selected from the group consisting of a methylation marker, an acetylation marker, and a phosphorylation marker.

11. The method of claim 4, wherein said marker is phosphorylated H3T11.

* * * * *

SEQUENCE LISTING

<160> NUMBER OF SEQ ID NOS: 7

<210> SEQ ID NO 1
<211> LENGTH: 102
<212> TYPE: PRT
<213> ORGANISM: Artificial Sequence
<220> FEATURE:
<223> OTHER INFORMATION: Chemically synthesized

<400> SEQUENCE: 1

```
Ser Gly Arg Gly Lys Gly Gly Lys Gly Leu Gly Lys Gly Gly Ala Lys
  1               5                  10                  15

Arg His Arg Lys Ile Leu Arg Asp Asn Ile Gln Gly Ile Thr Lys Pro
             20                  25                  30

Ala Ile Arg Arg Leu Ala Arg Arg Gly Gly Val Lys Arg Ile Ser Gly
         35                  40                  45

Leu Ile Tyr Glu Glu Val Arg Ala Val Leu Lys Ser Phe Leu Glu Ser
     50                  55                  60

Val Ile Arg Asp Ser Val Thr Tyr Thr Glu His Ala Lys Arg Lys Thr
 65                  70                  75                  80

Val Thr Ser Leu Asp Val Val Tyr Ala Leu Lys Arg Gln Gly Arg Thr
                 85                  90                  95

Leu Tyr Gly Phe Gly Gly
            100
```

<210> SEQ ID NO 2
<211> LENGTH: 135
<212> TYPE: PRT
<213> ORGANISM: Artificial Sequence
<220> FEATURE:
<223> OTHER INFORMATION: Chemically synthesized

<400> SEQUENCE: 2

```
Ala Arg Thr Lys Gln Thr Ala Arg Lys Ser Thr Gly Gly Lys Ala Pro
  1               5                  10                  15

Arg Lys Gln Leu Ala Ser Lys Ala Ala Arg Lys Ser Ala Pro Ser Thr
             20                  25                  30

Gly Gly Val Lys Lys Pro His Arg Tyr Lys Pro Gly Thr Val Ala Leu
         35                  40                  45

Arg Glu Ile Arg Arg Phe Gln Lys Ser Thr Glu Leu Leu Ile Arg Lys
     50                  55                  60

Leu Pro Phe Gln Arg Leu Val Arg Glu Ile Ala Gln Asp Phe Lys Thr
 65                  70                  75                  80

Asp Leu Arg Phe Gln Ser Ser Ala Ile Gly Ala Leu Gln Glu Ser Val
                 85                  90                  95

Glu Ala Tyr Leu Val Ser Leu Phe Glu Asp Thr Asn Leu Ala Ala Ile
                100                 105                 110

His Ala Lys Arg Val Thr Ile Gln Lys Lys Asp Ile Lys Leu Ala Arg
            115                 120                 125

Arg Leu Arg Gly Glu Arg Ser
        130                 135
```

<210> SEQ ID NO 3
<211> LENGTH: 13
<212> TYPE: PRT
<213> ORGANISM: Artificial Sequence
<220> FEATURE:
<223> OTHER INFORMATION: Chemically synthesized -continued

```
<400> SEQUENCE: 3

Glu His Ala Lys Arg Lys Thr Val Thr Ser Leu Asp Val
1               5                  10

<210> SEQ ID NO 4
<211> LENGTH: 16
<212> TYPE: PRT
<213> ORGANISM: Artificial Sequence
<220> FEATURE:
<223> OTHER INFORMATION: Chemically synthesized

<400> SEQUENCE: 4

Leu Val Arg Glu Ile Ala Gln Asp Phe Lys Thr Asp Leu Arg Phe Gln
1               5                  10                  15

<210> SEQ ID NO 5
<211> LENGTH: 20
<212> TYPE: PRT
<213> ORGANISM: Artificial Sequence
<220> FEATURE:
<223> OTHER INFORMATION: Chemically synthesized

<400> SEQUENCE: 5

Tyr Lys Pro Gly Thr Val Ala Leu Arg Glu Ile Arg Arg Phe Gln Lys
1               5                  10                  15

Ser Thr Glu Leu
            20

<210> SEQ ID NO 6
<211> LENGTH: 30
<212> TYPE: PRT
<213> ORGANISM: Artificial Sequence
<220> FEATURE:
<223> OTHER INFORMATION: Chemically synthesized

<400> SEQUENCE: 6

Ser Gly Arg Gly Lys Gly Gly Lys Gly Leu Gly Lys Gly Gly Ala Lys
1               5                  10                  15

Arg His Arg Lys Ile Leu Arg Asp Asn Ile Gln Gly Ile Thr
            20                  25                  30

<210> SEQ ID NO 7
<211> LENGTH: 41
<212> TYPE: PRT
<213> ORGANISM: Artificial Sequence
<220> FEATURE:
<223> OTHER INFORMATION: Chemically synthesized

<400> SEQUENCE: 7

Ala Arg Thr Lys Gln Thr Ala Arg Lys Ser Thr Gly Gly Lys Ala Pro
1               5                  10                  15

Arg Lys Gln Leu Ala Ser Lys Ala Ala Arg Lys Ser Ala Pro Ser Thr
            20                  25                  30

Gly Gly Val Lys Lys Pro His Arg Tyr
            35                  40
```